United States Patent [19]

Braune

[11] Patent Number: 5,789,500
[45] Date of Patent: Aug. 4, 1998

[54] PROCESS FOR PREPARING RESIDUES CONTAINING DIHYDROXY COMPOUNDS

[75] Inventor: Peter Braune, Erbes-Büdesheim, Germany

[73] Assignee: BASF Aktiengesellschaft, Ludwigshafen, Germany

[21] Appl. No.: 894,954

[22] PCT Filed: Mar. 6, 1997

[86] PCT No.: PCT/EP96/00940

§ 371 Date: Sep. 4, 1997

§ 102(e) Date: Sep. 4, 1997

[87] PCT Pub. No.: WO96/29358

PCT Pub. Date: Sep. 26, 1996

[30] Foreign Application Priority Data

Mar. 18, 1995 [DE] Germany ............... 195 09 957.5

[51] Int. Cl.$^6$ .................. C08F 2/00; C08G 65/00
[52] U.S. Cl. .............. 526/67; 528/272; 528/501; 528/503; 526/65; 526/66; 526/68
[58] Field of Search ............... 528/272, 501, 528/503; 526/65, 66, 67, 68

[56] References Cited

U.S. PATENT DOCUMENTS

| | | |
|---|---|---|
| 4,110,316 | 8/1978 | Edging et al. |
| 4,239,882 | 12/1980 | Kimura et al. |
| 4,499,261 | 2/1985 | Heinze et al. |
| 5,236,558 | 8/1993 | Buyalos et al. |

FOREIGN PATENT DOCUMENTS 2 045 752   11/1980   United Kingdom .

OTHER PUBLICATIONS

Ulmanns Encyklopadie ... Band 19,61–88.

Chemiefasern/Textilindustrie 40 (1992), 1058–1062.

*Primary Examiner*—Samuel A. Acquah
*Attorney, Agent, or Firm*—Keil & Weinkauf

[57] ABSTRACT

A process for working up dihydroxy compound residues from the preparation of polyesters by a) a first step of (trans)esterifying a dicarboxylic acid or its esters or ester-forming derivatives with a molar excess of a dihydroxy compound, b) at least one second step of polycondensing the esterification product of a), and c) subjecting the vapors from the reaction of a) and b) to a treatment for recovering the starting materials, comprises 1) combining the vapors of step a) and some of the vapors of step b) of the process in at least one column A) and removing the low boiling constituents of the vapors overhead and recycling the bottom product, which predominantly contains the excess dihydroxy compounds and also oligomeric and polymeric reaction products, into step a), and 2) transferring the other part of the vapors of step b) of the process into at least one column B) and removing the low boiling constituents of the vapors overhead and discharging the bottom product from the column and subsequently subjecting it to a further treatment for recovering the dihydroxy compound.

3 Claims, 1 Drawing Sheet

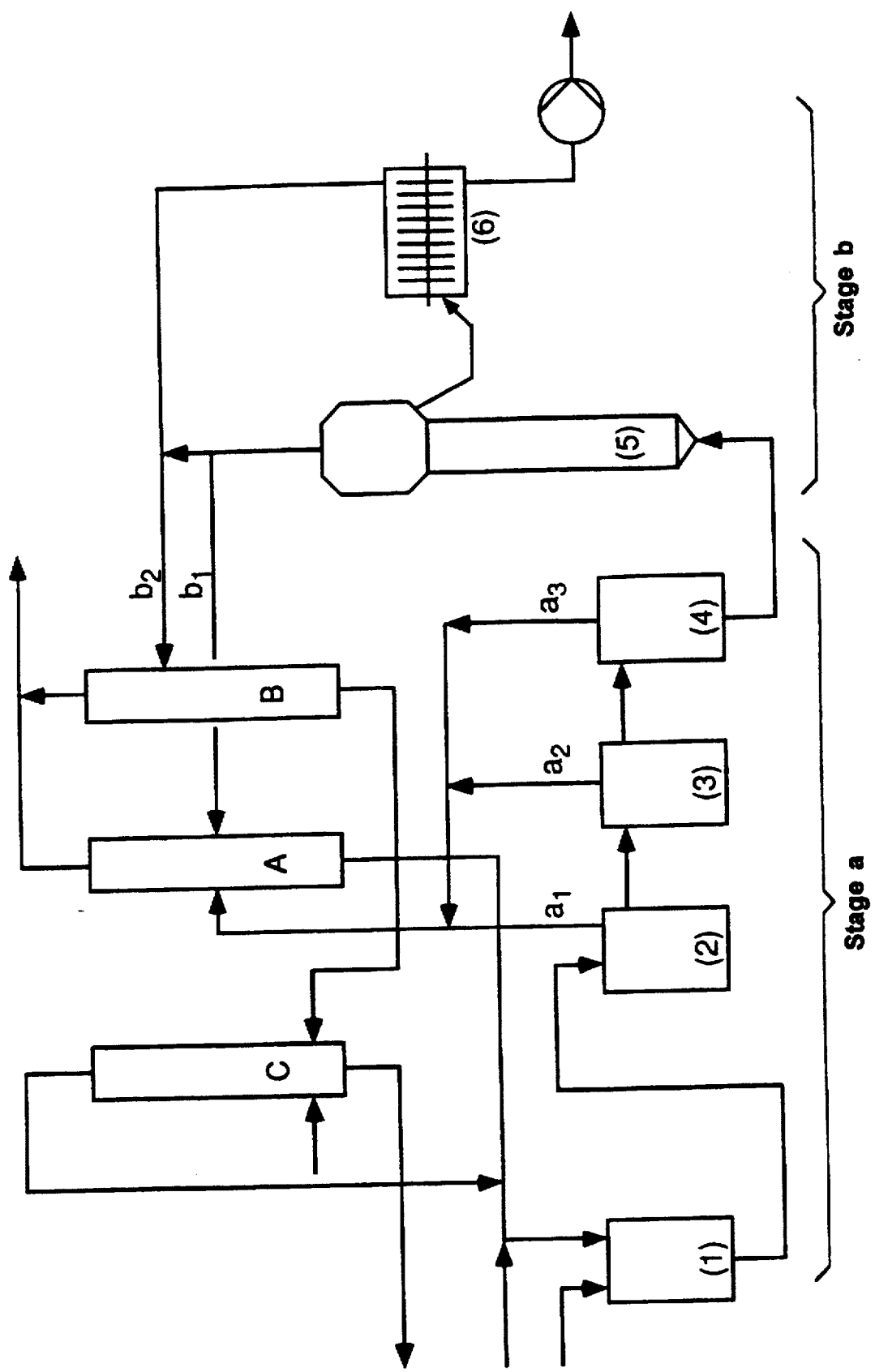

PROCESS FOR PREPARING RESIDUES CONTAINING DIHYDROXY COMPOUNDS

The present invention relates to processes for working up dihydroxy compound residues from the preparation of polyesters by a) a first step of (trans)esterifying a dicarboxylic acid or its esters or ester-forming derivatives with a molar excess of a dihydroxy compound, b) at least one second step of polycondensing the esterification product of a), and c) subjecting the vapors from the reaction of a) and b) to a treatment for recovering the starting materials.

Polyesters, especially polyalkylene terephthalates, are widely prepared using (trans)esterification/polycondensation processes in which a first stage involves an esterification or transesterification and the actual polycondensastion is carried out in one or more further stages (cf. Chemiefasern/Textilindustrie 40 (1992), 1058–1062, and Ullmann's Enzyklopädie der technischen Chemie, 4th edition, vol. 19, pages 61–88).

BRIEF DESCRIPTION

This process will now be briefly explained by way of example with reference to the preparation of polybutylene terephthalate from terephthalic acid and 1,4-butanediol.

In a first reaction space, terephthalic acid is esterified with a molar excess, preferably 50–120 mol %, in particular 70–100 mol %, of 1,4-butanediol, and the esterified compound is subjected to the actual polycondensation in further steps. The vapors from the esterification are transferred into a column in which the low boiling THF/water are removed overhead to leave a bottom product which, as well as excess 1,4-butanediol, additionally contains small amounts of oligomers, polymers and terephthalic acid.

The esterification product is subsequently polycondensed, advantageously in the case of continuous processes in at least two stages, a precondensation and a postcondensation.

For economic reasons it is desirable in this connection for as many as possible of the resulting reaction products and dihydroxy compounds present in excess to be further treated, for example in order to recover the 1,4-butanediol and to minimize waste.

In the preparation of polyesters, it is customary to work up the vapors from the polycondensation separately or not at all. It is not desirable to recycle the vapors into the esterification even after removal of the low boilers, since bottom products of this type have an excessive solids content. This solids content (oligomeric and polymeric constituents of the vapors) leads to a reduction in product quality due to fisheyes in the polyester. Fisheyes are higher melting, gellike particles which, for example, are the cause of nodules or breakages in fibermaking or of visible defects in film making.

With terephthalic acid as one of the starting materials there is the additional problem that the esterification requires a significantly larger excess of butanediol in order to shift the equilibrium of the ester reaction to the desired extent. The vapors from the polycondensation, especially the precondensation, contain a significantly larger proportion of the excess diol than the vapors from the esterification.

It is an object of the present invention to remedy the above-described disadvantages and to improve the workup of the vapors to the effect that most of the dihydroxy compounds present therein can be recycled into the esterification and that, based on the total amount of diol used, the loss of diol is minimized. At the same time, the product quality of the polyester shall be preserved.

We have found that this object is achieved, surprisingly, by 1) combining the vapors of step a) and some of the vapors of step b) of the process in at least one column A) and removing the low boiling constituents of the vapors overhead and recycling the bottom product, which predominantly contains the excess dihydroxy compounds and also oligomeric and polymeric reaction products, into step a), and 2) transferring the other part of the vapors of step b) of the process into at least one column B) and removing the low boiling constituents of the vapors overhead and discharging the bottom product from the column and subsequently subjecting it to a further treatment for recovering the dihydroxy compound.

The splitting of the vapors from the polycondensation is a technically simple way of achieving a recycle of the excess diol into the esterification. The process is more economical and less costly as a result, and the product quality of the polyester is preserved.

In what follows the process of this invention will again be explained by way of example with reference to the preparation of polybutylene terephthalate and with reference to the drawing; however, it may be emphasized once more that the process is also suitable for preparing other polyesters known to one skilled in the art.

First, terephthalic acid and 1,4-butanediol (the latter in an excess of 150–220 mol %, preferably 70–100 mol %) are reacted with each other in a conventional manner at temperatures within the range from 150° to 220° C. and pressures within the range from 0.7 to 1.5 bar over a period of from 30 to 90, preferably from 40 to 70, minutes. An esterification takes place and resulting THF (tetrahydrofuran) together with excess butanediol (BD) and small amounts of oligomeric and polymeric compounds and also residual terephthalic acid are transferred with the vapors ($a_1$, $a_2$ and $a_3$) into a column A). The point of addition is preferably located in the middle or the lower part of the column.

Stage a) of the process is subdivided in the drawing into 4 process steps, illustrated with the stirred reactors (1) to (4), which constitutes a particularly preferred embodiment of stage a).

The esterification product of stage a) of the process is polycondensed in at least one second stage b). This polycondensation is carried out in a conventional manner at temperatures of from 240° C. to 270° C. and reduced pressure of from 0.3 to 200 mbar over a period of from 60 to 200, preferably from 70 to 180, minutes. The drawing illustrates a particularly preferred embodiment of stage b), represented by the reactors (5) and (6), a precondensation being carried out in (5) and a postcondensation in (6).

The vapors from stage b) (depicted in the drawing as ($b_1$) and ($b_2$)), which predominantly contain THF, water, excess butanediol and somewhat larger amounts than in the vapors from stage a) of oligomeric and polymeric compounds and also residual quantities of terephthalic acid, are transferred in proportion into columns A) and B), column A) already containing the vapors from stage a) of the process. The point of addition is preferably located in the middle or the lower part of the columns. It will be appreciated that the determining of the proportions depends on the fill volumes of the columns and the feedstocks required in the esterification.

In column A) of the process of this invention, the low boiling THF/water is removed overhead and these low boiling constituents are subsequently subjected to a recovery of the starting materials (separation of THF from water).

In the case of the preparation of polyethylene terephthalate, the low boiling constituents consist essentially of water and acetaldehyde; in the case of the preparation of PBT from dimethyl terephthalate they consist essentially of methanol and water. Thereafter the bottom product, which predominantly contains the excess dihydroxy compounds, is recycled into stage a) (reactor (1)). The other part of the vapors from stage b) of the process is transferred into at least one column B). Depending on the size of the plant, columns A) and B) can be subdivided into a plurality of columns $A_1$, $A_2$ to $A_n$ or $B_1$, $B_2$ to $B_n$.

The low boiling constituents of the vapors ($b_2$ from stage b) are removed overhead and the bottom product is discharged and subsequently subjected to a further treatment for recovering the dihydroxy compound. For this, the bottom product is discharged to a column C) with removal of the solids.

Preferably, column C) is fed at the same time with a liquid dihydroxy compound residue ("hex") as obtained for example from the distillation of 1,4-butanediol or 1,6-hexanediol. The composition of the residue is not subject to any special restriction, as long as it is liquid and does not contain any compounds which might interfere with the separation in the column. This is generally the case with residues from the distillation of butanediol or hexanediol.

The point of addition is preferably located in the middle or the lower part of the column, and the rate of addition is generally within the range from 0.03 to 3 kg per kg of bottom products conferred to the column, preferably within the range from 0.04 to 0.1 kg/kg.

As a consequence of the addition of this dihydroxy compound residue, the bottom products in column C) remain liquid or conveyable, and it is therefore technically simple to obtain the hydroxy compound overhead and again a liquid or conveyable bottom product at the base of this column, which is simple to carry off to an incineration.

The dihydroxy compound is then recycled into the esterification (stage a).

The advantages of the process of this invention are that very large proportions of the vapors can be recycled into the esterification in a simple manner. This results in a further simplification and cost saving without impairing the product quality.

EXAMPLE

In a stirred tank cascade, 306 kg/h of terephthalic acid, 332 kg/h of butanediol (molar ratio 1:2) and 30 ppm of Ti as tetrabutyl orthotitanate, based on 1 kg of PBT (catalyst), were esterified at a temperature of 230° C. and a pressure of 1 bar with an average residence time of 205 minutes. The vapors from the esterification were continuously transferred into a column A). The esterification product was transferred with a conversion of >95% into polycondensation stage b). Vapors from stage b) were continuously transferred into 2 columns so that 56% were combined in column A) with the vapors from the stage a) and 44% were transferred into a column B).

Workup column A)

First, THF and $H_2O$ were separated overhead from the vapors of stages a) and b) and the bottom product was recycled into the esterification with a throughput of 167 kg/h.

Workup column B)

First THF and $H_2O$ (low boilers) were separated overhead from the part of vapors from stage b) of the process, and the bottom product was transferred with a throughput of 58 kg/h and removal of the solids into a column C) fed, at a point located in the middle thereof, with 4 kg/h of a liquid residue from the distillation of 1,4-butanediol, containing mainly 1,4-butanediol, 2-methyl-1,5-pentanediol, 1,6-hexanediol, 2-methyl-1,6-hexanediol and 1,2,5-pentanetriol.

Butanediol was removed at the top of column C) and a liquid bottom product was removed at the base of the column. The bottom product was piped into an incineration facility.

The workup according to this invention recycled 56 mol % of the 100% molar excess of butanediol into a stage a) after removal of low boilers. 44 mol % were recovered by distillation. These mol % ages are based on the BD excess following removal of the THF fraction. 20 mol % of the butanediol equivalent are customarily converted by the reaction into THF and water (the butanediol equivalent is the theoretical molar fraction required for the reaction). The bottom product fed to the incinerating unit contained 63% of the residue from the butanediol distillation ("hex"), 18.5% of solid residues (oligomeric/polymeric fractions) and 18.5% of butanediol from the reaction. These 18.5% of butanediol in the residue were merely 2% of the total amount of butanediol introduced into column C). Thus, a total of 0.35% of butanediol was lost, based on the butanediol used in the esterification (TPA: BD=1:2 mol).

We claim:

1. A process for working up dihydroxy compound residues from the preparation of polyesters by a) a first step of (trans)esterifying a dicarboxylic acid or its esters or ester-forming derivatives with a molar excess of a dihydroxy compound, b) at least one second step of polycondensing the esterification product of a), and c) subjecting the vapors from the reaction of a) and b) to a treatment for recovering the starting materials, which comprises 1) combining the vapors of step a) and some of the vapors of step b) of the process in at least one column A) and removing the low boiling constituents of the vapors overhead and recycling the bottom product, which predominantly contains the excess dihydroxy compounds and also oligomeric and polymeric reaction products, into step a), and 2) transferring the other part of the vapors of step b) of the process into at least one column B) and removing the low boiling constituents of the vapors overhead and discharging the bottom product from the column and subsequently subjecting it to a further treatment for recovering the dihydroxy compound.

2. A process as claimed in claim 1 wherein the low boiling constituents of the vapors consist essentially of water, tetrahydrofuran, acetaldehyde and methanol.

3. A process as claimed in claim 1 wherein the bottom product of column B) is discharged into a column C) with removal of the solids, a liquid dihydroxy compound residue is added, and subsequently a treatment for recovering the hydroxy compound is carried out.

* * * * *

UNITED STATES PATENT AND TRADEMARK OFFICE
CERTIFICATE OF CORRECTION

PATENT NO.: 5,789,500

DATED: August 4, 1998

INVENTOR(S): Peter BRAUNE

It is certified that error appears in the above-identified patent and that said Letters Patent is hereby corrected as shown below:

On the cover sheet, item [22], correct the PCT filing date to read: --Mar. 6, 1996--.

Signed and Sealed this

Twenty-seventh Day of October, 1998

*Attest:*

BRUCE LEHMAN

*Attesting Officer*     *Commissioner of Patents and Trademarks*